United States Patent [19]

Mertens et al.

[11] Patent Number: 5,599,826
[45] Date of Patent: Feb. 4, 1997

[54] THIAZOLIDINEDIONES AND DRUGS CONTAINING THEM

[75] Inventors: Alfred Mertens, Schriesheim; Hans-Peter Wolff, Mannheim; Peter Freund, Ketsch, all of Germany

[73] Assignee: Boehringer Mannheim GmbH, Mannheim, Germany

[21] Appl. No.: 578,561

[22] PCT Filed: May 19, 1994

[86] PCT No.: PCT/EP94/01619

§ 371 Date: Nov. 21, 1995

§ 102(e) Date: Nov. 21, 1995

[87] PCT Pub. No.: WO94/27995

PCT Pub. Date: Dec. 8, 1994

[30] Foreign Application Priority Data

May 25, 1993 [DE] Germany ............... 43 17 320.9

[51] Int. Cl.⁶ ............... C07D 417/12; A61K 31/425
[52] U.S. Cl. ............... 514/364; 514/342; 546/146; 546/175; 546/122; 546/269.7; 546/270.4; 548/181; 548/183
[58] Field of Search ............... 548/181, 183; 546/146, 175, 280; 514/364, 342

[56] References Cited

FOREIGN PATENT DOCUMENTS

| | | |
|---|---|---|
| 207605 | 1/1987 | European Pat. Off. |
| 299620 | 1/1989 | European Pat. Off. |
| 559571 | 9/1993 | European Pat. Off. |
| 8908052 | 9/1989 | WIPO |
| 9200967 | 9/1992 | WIPO |

*Primary Examiner*—Robert Gerstl
*Attorney, Agent, or Firm*—Nikaido, Marmelstein, Murray & Oram LLP

[57] ABSTRACT

Compounds of formula I

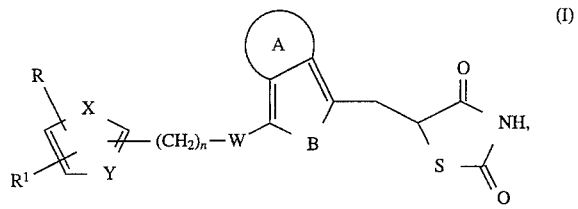

in which

A denotes a carbocyclic ring with 5 or 6 carbon atoms or a heterocyclic ring with a maximum of 4 heteroatoms in which the heteroatoms can be the same or different and denote oxygen, nitrogen or sulphur and the heterocycles can if desired carry an oxygen atom on one or several nitrogen atoms, B denotes —CH=CH—, —N=CH—, —CH=N—, O or S, W denotes $CH_2$, O, CH(OH), CO or —CH=CH—, X denotes S, O or $NR^2$ in which the residue $R^2$ is hydrogen or $C_1$–$C_6$ alkyl, Y is CH or N, R denotes naphthyl, pyridyl, furyl, thienyl or phenyl which if desired is mono- or disubstituted with $C_1$–$C_3$ alkyl, $CF_3$, $C_1$–$C_3$ alkoxy, F, Cl or bromine, $R^1$ denotes hydrogen or $C_1$–$C_6$ alkyl and n equals 1–3
as well as their tautomers, enantiomers, diastereomers and physiologically tolerated salts,
processes for their production as well as pharmaceutical agents that contain these compounds for the treatment of diabetes.

13 Claims, No Drawings

THIAZOLIDINEDIONES AND DRUGS CONTAINING THEM

This application is a 371 of PCT/EP94/01619 filed May 19, 1994.

The present invention concerns thiazolidinediones, processes for their production and pharmaceutical agents which contain these compounds.

The invention concerns thiazolidinediones of the general formula I

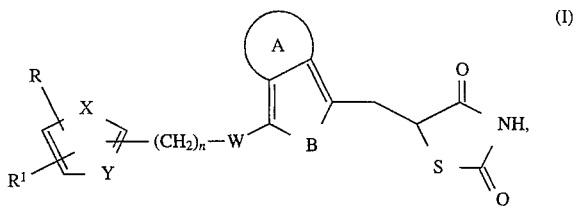

in which
- A denotes a carbocyclic ring with 5 or 6 carbon atoms or a heterocyclic ring with a maximum of 4 heteroatoms in which the heteroatoms can be the same or different and denote oxygen, nitrogen or sulphur and the heterocycles can if desired, carry an oxygen atom on one or several nitrogen atoms,
- B denotes —CH=CH—, —N=CH—, —CH=N—, O or S,
- W denotes $CH_2$, O CH(OH), CO or —CH=CH—,
- X denotes S, O or $NR^2$ in which the residue $R^2$ is hydrogen or $C_1$–$C_6$ alkyl,
- Y is CH or N,
- R denotes naphthyl, pyridyl, furyl, thienyl or phenyl which if desired is mono- or disubstituted with $C_1$–$C_3$ alkyl, $CF_3$, $C_1$–$C_3$ alkoxy, F, Cl or bromine,
- $R^1$ denotes hydrogen or $C_1$–$C_6$ alkyl and
- n equals 1–3 as well as their tautomers, enantiomers, diastereomers and physiologically tolerated salts.

Similar compounds with anti-diabetic action have already been mentioned in the literature. Thus thiazolidine-diones with a hypoglycaemic action are described in the application U.S. Pat. No. 4,617,312 in which an alkoxy residue is absolutely necessary in the ortho position relative to the thiazolidinedione. The synthesis of 5-[4-(2-methyl-2-phenyl-propoxy)benzyl]thiazolidine-2,4-diones and their anti-diabetic action is presented in Chem. Pharm. Bull., 30, 3563, 1982. The U.S. Pat. Nos. 4,340,605, 4,725,610 and EP-A-389699 encompass 4-alkoxybenzylthiazolidine-diones with a hypoglycaemic action which are substituted by a heterocycle in the alkyl moiety. The European Application EP-A-332332 also claims an anti-diabetic action for benzyl-thiazolidinediones which can be substituted by various residues in the para position.

The U.S. Pat. No. 4,703,052 describes anti-diabetic derivatives which are linked with a bicycle in which, however, the aromatic ring of the bicycle which carries the thiazolidine residue may not contain any further substituent. The European Patent Applications EP-A-283035 and EP-A-299620 encompass benzoxazole-linked and benzofuran-linked thiazolidinediones with an anti-diabetic action.

It has now been surprisingly found that aromatic rings which are substituted in the same ring system by a thiazolidinedione residue and by a further substituent and to which in addition an aromatic five-membered or six-membered ring is condensed, have valuable pharmacological properties.

The compounds according to the invention are particularly suitable for the production of anti-diabetics for the oral treatment of diabetes mellitus and in particular of type II or type IIb. According to present knowledge an impairment in the utilization of insulin and glucose plays an important role in this as one of the main causes of diabetes of old age. This impairment in the utilization causes a hyperinsulinaemia which in turn is considered to be a risk factor for the development of macroangiopathic complications. Investigations on adipose type II diabetics showed that the substances according to the invention can be used to lower the level of glucose as well as of insulin. Due to their special mechanism of action the substances have some additional advantages: they do not cause hypoglycaemias and can lower the risk of arteriosclerosis in type II diabetics since they also reduce the insulin level. They are therefore also suitable for the prophylaxis of arteriosclerotic diseases. In addition they have a positive effect on elevated blood pressure values and lower the triglyceride and cholesterol level.

Preferred residues for the ring system A are carbocyclic rings with 5 or 6 carbon atoms or a heterocyclic five-membered or six-membered ring with 1 or 2 heteroatoms in which the heteroatoms can be the same or different and denote oxygen, nitrogen or sulphur.

The residues —CH=CH—, —N=CH— or —CH=N— are preferred for B.

W is preferably $CH_2$, O CH(OH) or CO.

X preferably denotes S, O or NH.

Y preferably denotes N.

Preferred residues for R are naphthyl, pyridyl, furyl, thienyl or phenyl which if desired are mono- or disubstituted with methyl, $CF_3$, methoxy, fluorine, chlorine or bromine.

Particularly preferred residues for A are carbocyclic aromatic rings with 6 carbon atoms or a heterocyclic aromatic five-membered or six-membered ring with one heteroatom in which the heteroatom can denote oxygen, nitrogen or sulphur. A is especially preferably a phenyl or pyridyl ring.

Particularly preferred residues for B are —CH=CH, —N=CH— and —CH=N—.

O CH(OH) and CO are considered to be particularly preferable for W.

X particularly preferably has the meaning S or O.

Particularly preferred residues for R are pyridyl, furyl, thienyl or phenyl which if desired are mono- or disubstituted by methyl, methoxy, fluorine or chlorine. In this case phenyl, methylphenyl, methoxyphenyl, fluorophenyl or chlorophenyl are especially preferred.

Hydrogen, methyl or ethyl are especially preferred for $R^1$.

n is particularly preferably 2.

In order to produce pharmaceutical agents, the compounds of the general formula I are mixed in a known manner with suitable pharmaceutical carrier substances, aromatics, flavourings and dyes and are formed for example into tablets or coated tablets or they are suspended or dissolved in water or an oil such as e.g. olive oil with addition of appropriate auxiliary substances.

The substances of the general formula I can be administered orally or parenterally in a liquid or solid form. Water is preferably used as the injection medium which contains the stabilizing agents, solubilizers and/or buffers which are usually used for injection solutions. Such additives are for example tartrate or borate buffers, ethanol, dimethylsulfoxide, complexing agents (such as ethylenediaminetetraacetic acid), high molecular polymers (such as liquid polyethylene oxide) for the regulation of the viscosity or polyethylene derivatives of sorbitol anhydrides.

Solid carrier substances are e.g. starch, lactose, mannitol, methylcellulose, talcum, highly dispersed silicic acid, higher molecular fatty acids (such as stearic acid), gelatin, agar-agar, calcium phosphate, magnesium stearate, animal and vegetable fats or solid high molecular polymers (such as polyethylene glycols). Suitable formulations for the oral application can if desired contain flavourings and sweeteners.

The administered dose depends on the age, the health and the weight of the recipient, the extent of the disease, the type of treatments which are possibly being carried out concurrently, the frequency of the treatment and the type of the desired effect. The daily dose of the active compound is usually 0.1 to 50 mg/kg body weight. Normally 0.5 to 40 and preferably 1.0 to 20 mg/kg/day in one or several applications per day are effective in order to obtain the desired results.

The compounds according to the invention of the general formula I are produced according to processes known in the literature (J. Med. Chem. 35, 1835, 1992 J. Med. Chem. 35, 2617, 1992, Chem. Pharm. Bull. 30, 3580, 1982, Chem. Pharm. Bull 30, 3563, 1982) in which a) compounds of the general formula II

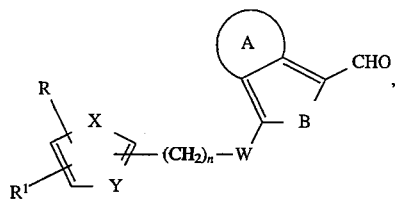

in which A, B, W, X, Y, R, $R^1$ and n have the aforementioned meanings are reacted with thiazolidinediones to form compounds of the general formula III

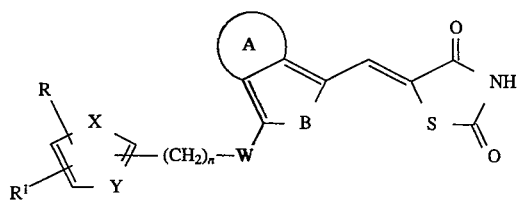

in which A, B, W, X, Y, R, $R^1$ and n have the aforementioned meanings and subsequently compounds of the general formula I are obtained by reduction of the double bond, or b) compounds of the general formula IV

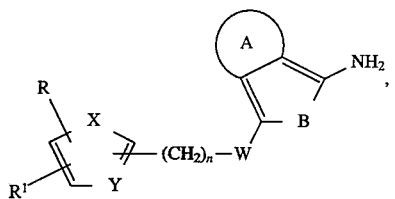

in which A, B, W, X, Y, R, $R^1$ and n have the aforementioned meanings are reacted with $NaCO_2$ in the presence of acrylic ester and HCl or HBr to form compounds of the general formula V

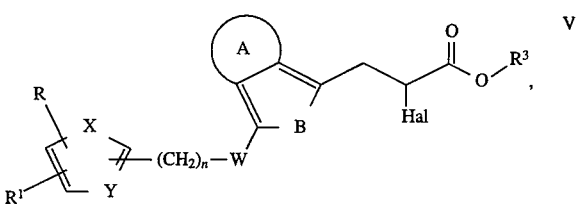

in which A, B, W, X, Y, R, $R^1$ and n have the aforementioned meanings, Hal represents chlorine or bromine and $R^3$ denotes a $C_1$–$C_6$ alkyl residue and subsequently compounds of the general formula V are cyclised with thiourea to form compounds of the general formula VI

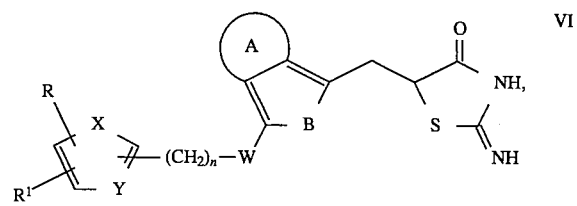

in which A, B, W, X, Y, R, $R^1$ and n have the aforementioned meanings and are converted into compounds of the general formula I by treatment with acid.

The reaction of compounds of the general formula II with thiazolidinedione is possible in polar and unpolar solvents to which if desired an auxiliary base such as e.g. sodium acetate or triethylamine is added at temperatures between −40° C. and the boiling point of the selected solvent. The subsequent reduction of compounds of the general formula III is preferably carried out with hydrogen in the presence of metal catalysts such as e.g. Pt of Pd or also by homogeneous catalysis in inert solvents at temperatures between −20° C. and the boiling point of the solvent. If desired, the catalytic hydrogenation can be accelerated by increasing the pressure.

The conversion of compounds of the general formula IV into compounds of the general formula V is preferably achieved in aqueous solvents containing $NaNO_2$ in the presence of acids such as e.g. hydrochloric acid and hydrobromic acid in which the diazonium salt which is formed as an intermediary is reacted with acrylic ester derivatives, if desired, with addition of Cu(I) salts.

These halogen—carboxylic acid esters can be advantageously converted into compounds of the general formula VI using urea in protic solvents at temperatures of −20° C. up to the boiling point of the solvent and if desired, with addition of an auxiliary base such as e.g. sodium acetate or $NEt_3$. Compounds of the general formula I are obtained from them by hydrolysis with addition of acids such as e.g. hydrochloric acid or with use of a lye such as e.g. sodium hydroxide preferably in a protic solvent which can be heated if necessary.

Pure enantiomers of compounds of formula I are formed either by racemate resolution (via salt formation with optically active acids or bases) or by using optically active starting materials in the synthesis.

Apart from the compounds mentioned in the examples and by combining all meanings of the substituents mentioned in the claims, the following compounds of formula I come into consideration within the scope of the present invention which can be present as racemic mixtures or in an optically active form such as pure R and S enantiomers:

1. 5-[4-[2-(5-methyl-2-phenyl-4-oxazolyl)ethoxy]-1-naphthylmethyl]-2,4-thiazolidinedione
2. 5-[7-[2-(5-methyl-2-phenyl-4-oxazolyl)ethoxy]-4-indolylmethyl]-2,4-thiazolidinedione 3. 5-[7-[2-(5-methyl-2-phenyl-4-oxazolyl)ethoxy]-4-benzofuranyl-methyl]-2,4-thiazolidinedione
4. 5-[7-[2-(5-methyl-2-phenyl-4-oxazolyl)ethoxy]-4-benzothiophenyl-methyl]-2,4-thiazolidinedione
5. 5-[4-[2-(5-methyl-2-phenyl-4-oxazolyl)ethoxy]-7-indolylmethyl]-2,4-thiazolidinedione
6. 5-[4-[2-(5-methyl-2-phenyl-4-oxazolyl)ethoxy]-7-benzofuranylmethyl-]-2,4-thiazolidinedione
7. 5-[4-[2-(5-methyl-2-phenyl-4-oxazolyl)ethoxy]-7-benzothiophenylmethyl]-2,4-thiazolidinedione
8. 5-[8-[2-(5-methyl-2-phenyl-4-oxazolyl)ethoxy]-5-quinolinylmethyl]-2,4-thiazolidinedione
9. 5-[8-[2-(5-methyl-2-phenyl-4-oxazolyl)ethoxy]-5-isoquinolinylmethyl]-2,4-thiazolidinedione
10. 5-[5-[2-(5-methyl-2-phenyl-4-oxazolyl)ethoxy]-8-isoquinolinylmethyl]-2,4-thiazolidinedione
11. 5-[5-[2-(5-methyl-2-phenyl-4-oxazolyl)ethoxy]-8-quinolinylmethyl]-2,4-thiazolidinedione
12. 5-[1-[2-(5-methyl-2-phenyl-4-oxazolyl)ethoxy]-4-isoquinolinylmethly]-2,4-thiazolidinedione
13. 5-[4-[2-(5-methyl-2-phenyl-4-oxazolyl)ethoxy]-1-isoquinolinylmethyl]-2,4-thiazolidinedione
14. 5-[4-[2-[5-methyl-2-(4-methylphenyl)-4-oxazolyl)ethoxy]-1-naphthylmethyl]-2,4-thiazolidinedione
15. 5-[4-[2-[5-methyl-2-(2-thienyl)-4-oxazolyl)ethoxy]-1-naphthylmethyl]-2,4-thiazolidinedione
16. 5-[4-[2-[5-methyl-2-(4-pyridyl)-4-oxazolyl)ethoxy]-1-naphthylmethyl]-2,4-thiazolidinedione
17. 5-[4-(5-methyl-2-phenyl-4-oxazolyl)methoxy]-1-naphthylmethyl]-2,4-thiazolidinedione
18. 5-[4-[3-(5-methyl-2-phenyl-4-oxazolyl)propionyl]-1-naphthylmethyl]-2,4-thiazolidinedione
19. 5-[4-[3-(5-methyl-2-phenyl-4-oxazolyl)1-hydroxypropyl]-1-naphthylmethyl]-2,4-thiazolidinedione
20. 5-[4-[2-(5-methyl-2-phenyl-4-oxazolyl)acetyl]-1-naphthylmethyl]-2,4-thiazolidinedione
21. 5-[4-[2-(5-methyl-2-phenyl-4-thiazolyl)ethoxy]-1-naphthylmethyl]-2,4-thiazolidinedione
22. 5-[4-[2-(5-methyl-2-phenyl-4-imidazolyl)ethoxy]-1-naphthylmethyl]-2,4-thiazolidinedione

EXAMPLE 1

5-[4-[2-(5-methyl-2-phenyl-4-oxazolyl)ethoxy]-1-naphthylmethyl]-2,4-thiazolidinedione a) 8.6 g (0.05 mol) 4-hydroxynaphthalene-1-aldehyde, 13.07 g (0.05 mol) 5-methyl-2-phenyl-4-(2-bromoethyl)-oxazole and 3.4 g (0.05 mol) NaOEt were heated for 16 hours in 100 ml ethanol under reflux. It was subsequently concentrated by evaporation, the residue was taken up in $CH_2Cl_2$, dried and concentrated. After crystallization from isopropanol, 5.2 g 4-[2-(5-methyl-2-phenyl-4-oxazolyl)ethoxy]-naphthalene-1-aldehyde of melting point 130°–133° C. is obtained.

b) 5.07 g (0.014 mol) of the previous compound, 3.87 g (0.042 mol) thiazolidinedione and 0.28 ml piperidine are refluxed for 8 hours in 150 ml ethanol. After cooling, the precipitate was isolated by suction filtration, washed with ether and heated briefly with 50 ml ethyl acetate to 50° C. After addition of 100 ml ether, it was again suction filtered and the residue was washed with ether. 3.28 g 5-[4-[2-(5-methyl-2-phenyl-4-oxazolyl)ethoxy]naphthyl]methylene]-2,4-thiazolidinedione of melting point 248°–250° C. is obtained.

c) 456 mg of the previous compound was catalytically hydrogenated in 40 ml THF in the presence of 200 mg Pd/C (10%) within 36 hours at 50° C. and 6 bar. After separating the catalyst and evaporating the solvent, 265 mg of the title compound of melting point 188°–191° C. is obtained after crystallization from ethanol.

EXAMPLE 2 a) The title compound 5-[4-[2-[5-methyl-2-(4-pyridyl)-4-oxazolyl]ethoxy]-1-naphthylmethyl]-2,4-thiazolidinedione of melting point 238° C. (decomp.) is obtained analogously to example 1 starting with 5-methyl-2-(4-pyridyl-4-(2-bromoethyl)oxazole.

b) The title compound 5-[4-[2-[5-methyl-2-(2-thienyl)-4-oxazolyl]ethoxy]-1-naphthylmethyl]-2,4-thiazolidinedione of melting point 159°–162° C. is obtained analogously to example 1 starting with 5-methyl-2-(2-thienyl)-4-(2-bromoethyl)oxazole.

EXAMPLE 3

5-[4-[2-(5-methyl-2-phenyl-4-oxazolyl]ethoxy]-8-benzothiophenemethyl]-2,4-thiazolidinedione a) 5.15 g (0.034 mol) 4-hydroxybenzothiophene was dissolved in 130 ml methylethylketone and admixed with 9.4 g (0.068 mol) $K_2CO_3$ and 20 g (0.068 mol) 5-methyl-2-phenyl-4-(2-bromoethyl)oxazole. The preparation was boiled for 72 hours under reflux, evaporated, taken up in ethyl acetate and extracted three times by shaking with 2N NaOH. After cooling and evaporation of the organic phase, it was crystallized from ethyl acetate/isohexane. 8.8 g 4-[2-(5-methyl-2-phenyl-4-oxazolyl)ethoxy]benzothiophene of melting point 130°–132° C. is obtained.

b) 10 g (30 mmol) of the previous compound was nitrated in 30 ml glacial acetic acid using 1.3 ml (3 mmol) 100 percent $HNO_3$ while cooling. After 1 hour at 25° C., water was added, it was extracted with ethyl acetate, evaporated and the residue was purified by chromatography over silica gel (mobile solvent: heptane/methylethylketone 4:1). 4.1 g 4-[2-(5-methyl-2-phenyl-4-oxazolyl)-ethoxy]-8-nitrobenzothiophene of melting point 148°–149° C. is obtained.

c) 3.1 g (8.06 mmol) of the previous compound was hydrogenated in 150 ml THF with 0.6 g Pd/C 10%. After removing the catalyst and evaporating the solvent, 2.8 g 4-[2-(5-methyl-2-phenyl-4-oxazolyl)ethoxy]-8-aminobenzothiophene is obtained which was processed further without further purification.

d) 2.85 g (8.2 mmol) of the previous compound was suspended in 80 ml acetone and 3 ml 48 percent HBr. 0.55 g $NaNO_2$ in 4 ml water was added dropwise to this suspension at 0° C. After 15 minutes, 10.3 ml methyl acrylate was added dropwise and subsequently 20 mg CuBr was added at 10° C. The preparation warms up to 30° C. and is kept at this temperature for a further 1 hour. Subsequently it is evaporated, taken up in ethyl acetate, washed with water, cooled and again evaporated. The residue was purified by chromatography over silica gel (mobile solvent: heptane/methylethylketone 4:1). 1.2 g 3-[4-[-2-(5-methyl-2-phenyl-4-oxazolyl)ethoxy]-benzothiophen-8-yl-]-2-bromopropionic acid methyl ester of melting point 99°–100° C. is obtained.

e) 1 g (2 mmol) of the previous compound was boiled for 6 hours under reflux in 25 ml ethanol with 0.23 g thiourea and 0.16 g sodium acetate. It was subsequently evaporated, water/ether/isohexane was added to the residue and it was suction filtered. The solid residue was subsequently boiled for 5 hours under reflux with 20 ml 2N HCl and 30 ml ethylene glycol monoethyl ether. After evaporation, a bicarbonate solution was added, the precipitate was filtered by suction and triturated with ethyl acetate. 0.6 g of the title compound of melting point 200°–202° C. is obtained.

EXAMPLE 4

Description of the pharmacological experiments

The investigations described in the following were carried out on ob/ob mice. The ob/ob mouse is a model with the characteristics: hyperphagism, hyperglycaemia, hyperinsulinaemia and peripheral insulin resistance. This model is therefore particularly suitable for testing substances which have an effect on peripheral insulin resistance which according to current scientific opinion is causally involved in the development of type II diabetes.

The compounds of examples 1, 2a, 2b and 3 were tested in the aforementioned model. For this fed ob/ob mice were daily treated orally for 5 days with 100 mg/kg of the respective substance and a control group was treated only with the solubilizer methyl cellulose. The animals were sacrificed on the 5th day and the blood glucose concentration as well as the insulin concentration were determined in the collected blood. The blood glucose concentration was determined by means of the kinetic hexokinase method (Schmidt, F. H., Klin. Wschr. 39, 1244, 1961) using an EPOS-analyser 5060®, "Eppendorf Gerätebau", Hamburg. The insulin concentration was determined with a radioimmunoassay (Pharmacia Insulin-RIA 100) from the Pharmacia Diagnostics AB Uppsala, Sweden.

The results are shown in the attached table. Blood glucose$_{EndK}$ and insuling$_{EndK}$ represent the values of the concurrent control group after 5 days, the columns blood glucose and insulin represent the values obtained with the substances. The blood glucose-lowering and insulin-lowering effect of the compounds of examples 1, 2a, 2b and 3 can be clearly seen.

| Compound Example No. | Blood glucose$_{EndK}$ | Blood glucose | Insulin$_{EndK}$ | Insulin |
|---|---|---|---|---|
| 3 | 202 ± 14 | 105 ± 1** | 498 ± 34 | 84 ± 9** |
| 1 | 193 ± 16 | 129 ± 3** | 387 ± 36 | 59 ± 6** |
| 2a | 248 ± 41 | 187 ± 17 | 324 ± 46 | 366 ± 45 |
| 2b | | 135 ± 13** | 366 ± 45 | 95 ± 13** |

** = p < 0.01

We claim:
1. A compound of the formula

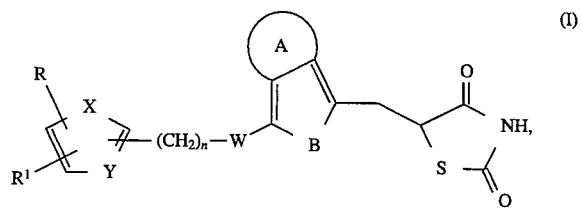

wherein

A is a carbocyclic ring of 5 or 6 carbon atoms or a 5 or 6-membered heterocyclic ring containing 1 or 2 heteroatoms, which heteroatoms are oxygen, nitrogen or sulfur, wherein each nitrogen atom independently carries no additional atoms or carries an oxygen atom;

B is —CH=CH=, —N=CH— or —CH=N—;

W is —CH$_2$—, —O—, —CH(OH)— or —CO—;

X is —S—, —O—, or —NH—;

Y is —N—;

R is naphthyl, pyridyl, furyl, thienyl or phenyl which are unsubstituted or substituted by one or two substituents, which are the same or different and are selected from the group consisting of C$_1$–C$_3$ alkyl, CF$_3$, C$_1$–C$_3$ alkoxy, F, Cl or Br;

R$^1$ is hydrogen or C$_1$–C$_6$ alkyl;

and n is 2;

and tautomers, enantiomers, diastereomers and pysiologically tolerated salts thereof.

2. Compound of claim 1, wherein A is a carbocyclic ring containing 6 carbon atoms.

3. Compound of claim 1, wherein A is a heterocyclic aromatic five-or six-member ring having one heteroatom which is oxygen, nitrogen or sulfur.

4. Compound of claim 1, wherein A is phenyl or pyridyl.

5. Compound of claim 1, wherein W is —O—, —CH(OH)— or —CO—.

6. Compound of claim 1, wherein X is —S— or —O—.

7. Compound of claim 1, wherein R is pyridyl, furyl, thienyl or phenyl which are unsubstituted or mono- or disubstituted by methyl, methoxy, fluorine or chlorine.

8. Compound of claim 7, wherein R is methoxyphenyl, methoxyphenyl, fluorophenyl or chlorophenyl.

9. Compound of claim 1, wherein R$^1$ is hydrogen, methyl or ethyl.

10. Compound of claim 1, wherein the compound is selected from the group consisting of 5-[4-9-2(5-methyl-2-phenyl-4-oxazolyl)ethoxy]-1-naphthylmethyl]- 2,4-thiazolidinedione 5-[4-[2-[5-methyl-2-(4-pyridyl)-4-oxazolyl]ethoxy]-1-naphthylmethyl]-2,4-thiazolidinedione 5-[4-[2-[5-methyl-2-(2-thienyl)-4-oxazolyl]ethoxy]-1-naphthylmethyl]-2,4-thiazolidinedione 5-[4-[2-(5-methyl-2-phenyl-4-oxazolyl]-ethoxy]-8-benzothiophenemethyl]-2,4-thiazolidinedione 5-[4-[2-(5-methyl-2-phenyl-4-oxazolyl)ethoxy]-1-naphthylmethyl]-2,4-thiazolidinedione 5-[7-[2-(5-methyl-2-phenyl-4-oxazolyl)ethoxy]-4-indolylmethyl]-2,4-thiazolidinedione 5-[7-[2-(5-methyl-2-phenyl-4-oxazolyl)ethoxy]-4-benzofuranyl-methyl]-2,4-thiazolidinedione 5-[7-[2-(5-methyl-2-phenyl-4-oxazolyl)ethoxy]-4-benzothiophenyl-methyl]-2,4-thiazolidinedione 5-[4-[2-(5-methyl-2-phenyl-4-oxazolyl)ethoxy]-7-indolylmethyl]-2,4-thiazolidinedione 5-[4-[2-(5-methyl-2-phenyl-4-oxazolyl)methoxy]-7-benzofuranylmethyl]-2,4-thiazolidinedione 5-[4-[2-(5-methyl-2-phenyl-4-oxazolyl)ethoxy]-7-benzothiophenylmethyl]-2,4-thiazolidinedione 5-[8-[2-(5-methyl-2-phenyl-4-oxazolyl)ethoxy]-5-quinolinylmethyl]-2,4-thiazolidinedione 5-[8-[2-(5-methyl-2-phenyl-4-oxazolyl)ethoxy]-5-isoquinolinylmethyl]-2,4-thiazolidinedione 5-[5-[2-(5-methyl-2-phenyl-4-oxazolyl)ethoxy]-8-isoquinolinylmethyl]-2,4-thiazolidinedione 5-[5-[2-(5-methyl-2-phenyl-4-oxazolyl)ethoxy]-8-quinolinylmethyl]-2,4-thiazolidinedione 5-[1-[2-(5-methyl-2-phenyl-4-oxazolyl)ethoxy]-4-isoquinolinylmethly]-2,4-thiazolidinedione 5-[4-[2-(5-methyl-2-phenyl-4-oxazolyl)ethoxy]-1-isoquinolinylmethyl]-2,4-thiazolidinedione 5-[4-[2-[5-methyl-2-(4-methylphenyl)-4-oxazolyl)ethoxy]-1-naphthylmethyl]-2,4-thiazolidinedione 5-[4-[2-[5-methyl-2-(2-thienyl)-4-oxazolyl)ethoxy]-1-naphthylmethyl]-2,4-thiazolidinedione 5-[4-[2-[5-methyl-2-(4-pyridyl)-4-oxazolyl)ethoxy]-1-naphthylmethyl]-2,4-thiazolidinedione 5-[4-(5-methyl-2-phenyl-4-oxazolyl)methoxy]-1-naphthylmethyl]-2,4-thiazolidinedione 5-[4-[3-(5-methyl-2-phenyl-4-oxazolyl)propionyl]-1-naphthylmethyl]-2,4-thiazolidinedione 5-[4-[3-(5-methyl-2-phenyl-4-oxazolyl)1-hydroxypropyl]-1-naphthylmethyl]-2,4-thiazolidinedione 5-[4-[2-(5-methyl-2-phenyl-4-oxazolyl)acetyl]-1-naphthylmethyl]-2,4-thiazolidinedione 5-[4-[2-(5-methyl-2-phenyl-4-thiazolyl)ethoxy]-1-naphthylmethyl]-2,4-thiazolidinedione 5-[4-[2-(5-methyl-2-phenyl-4-imidazolyl)ethoxy]-1-naphthylmethyl]-2,4-thiazolidinedione.

11. A pharmaceutical composition suitable for the treatment of diabetes comprising an antidiabetic effective amount of a compound of claim 1 and a pharmaceutically acceptable carrier.

12. A method of treating diabetes in a patient in need of such treatment, said method comprising administering to the patient of an antidiabetic effective amount of a compound of claim 1.

13. The compound according to claim 10, wherein the compound is:

5-4-[2-(5-methyl-2-phenyl-4-oxazolyl]ethoxy]-8-benzothiophenemethyl]-2,4-thiazolidinedione.

* * * * *

UNITED STATES PATENT AND TRADEMARK OFFICE
CERTIFICATE OF CORRECTION

PATENT NO. : 5,599,826
DATED : February 4, 1997
INVENTOR(S) : Mertens et al

It is certified that error appears in the above-identified patent and that said Letters Patent is hereby corrected as shown below:

Claim 1,
Line 9, change "-CH=CH=" to -- -CH=CH- --.

Claim 10,
Line 3, change "9-2" to -- [2-    --.
Line 9, change "8-ben" to -- 7-ben --.

Column 9,
Line 6, change "zothiophenylmethyl" to -- zothiophenemethyl --.

Claim 13,
Line 3, before "4", first occurrence, insert -- [ --.
Same line, change "8-ben" to -- 7-ben --.

SPECIFICATION:

Column 3,
Line 64, change "NACO$_2$" to -- NANO$_2$ --.

Column 5,
Line 11, change "zothiophenylmethyl" to -- zothiophenemethyl --.

UNITED STATES PATENT AND TRADEMARK OFFICE
CERTIFICATE OF CORRECTION

| | |
|---|---|
| PATENT NO. | : 5,599,826 |
| DATED | : February 4, 1997 |
| INVENTOR(S) | : Mertens et al |

It is certified that error appears in the above-identified patent and that said Letters Patent is hereby corrected as shown below:

<u>Column 6,</u>
Line 25, change "8-ben" to -- 7-ben --.
Line 46, change "8" to -- 7 --.
Line 52, change "8" to -- 7 --.
Line 67, change "8" to -- 7 --.

Signed and Sealed this

Seventh Day of August, 2001

*Attest:*

NICHOLAS P. GODICI
*Attesting Officer*     *Acting Director of the United States Patent and Trademark Office*